(12) United States Patent
Fors et al.

(10) Patent No.: US 8,725,535 B2
(45) Date of Patent: May 13, 2014

(54) SYSTEMS AND METHODS FOR USER-CONFIGURABLE RANGE SETTINGS IN CLINICAL INFORMATION SYSTEMS

(75) Inventors: Steve Lawrence Fors, Chicago, IL (US); Mark M. Morita, Arlington Heights, IL (US); William Douglas Hughes, Bainbridge Island, WA (US)

(73) Assignee: General Electric Company, Schenectady, NY (US)

( * ) Notice: Subject to any disclaimer, the term of this patent is extended or adjusted under 35 U.S.C. 154(b) by 1489 days.

(21) Appl. No.: 11/740,344

(22) Filed: Apr. 26, 2007

(65) Prior Publication Data

US 2008/0270187 A1 Oct. 30, 2008

(51) Int. Cl.
*G06Q 50/00* (2012.01)

(52) U.S. Cl.
USPC .................................. 705/3; 705/2

(58) Field of Classification Search
USPC ........................................ 705/2–3
See application file for complete search history.

(56) References Cited

U.S. PATENT DOCUMENTS

| | | | | |
|---|---|---|---|---|
| 4,896,291 A * | 1/1990 | Gest et al. | | 715/841 |
| 2001/0051879 A1 * | 12/2001 | Johnson et al. | | 705/2 |
| 2002/0082870 A1 * | 6/2002 | Penny et al. | | 705/3 |
| 2002/0161606 A1 * | 10/2002 | Bennett et al. | | 705/2 |
| 2004/0078240 A1 | 4/2004 | Katz | | |
| 2007/0016441 A1 | 1/2007 | Stroup | | |
| 2008/0004906 A1 | 1/2008 | Klass et al. | | |
| 2008/0186133 A1 * | 8/2008 | Parkhurst et al. | | 340/5.8 |
| 2008/0288288 A1 * | 11/2008 | Randazzo et al. | | 705/3 |

FOREIGN PATENT DOCUMENTS

EP 1862928 A1 5/2007

OTHER PUBLICATIONS

Roudenko, Virtual physical laboratory . . . , Russian Fed Nuclear Center, 2000.*
MediPATH, General Laboratory Managment, LRS Health, Jan. 1, 1988.*
TPS Australia, smartCHEM-LAB, 2002.*
American Thyroid Association, Thyroid function and obesity, Thyroid digest, Jul. 2006.*
Laboratory Module, Hospital Management Information System, 2005.*
Neelay et al, Autoverification of . . . , Clinical Laboratory Standards Institute, Jan. 1, 2006.*
Gest et al, U.S. Patent #4896291, Jan. 23, 1990.
MediPATH, General Laboratory Management, LRS Health, Jan. 1, 1988.
Randazzo, US Patent Application Pub #20080288268, Nov. 20, 2008.
Beckman Coulter, US Patent Application Pub #20080186133, Aug. 7, 2008.

* cited by examiner

*Primary Examiner* — Sind Phongsvirajati

(57) ABSTRACT

Certain embodiments of the present invention provide a clinical information system including a user interface and a custom range storage component. The user interface is adapted to allow a user to configure a custom range. The custom range is configured for a lab result. The custom range storage component adapted to store the configured custom range.

18 Claims, 3 Drawing Sheets

FIG. 2

⌐ DASHBOARD|INBOX|PATIENTS|ALERTS    ◯ Search

Quinn, Mona L · 51 f   ☐ Exam 19   DOB 9-15-1955   MRN 2718-A   HT 168cm   WT 83kg   ALLERGIES [1][2][2]

Care Team   Tasks(4)    Chart   Actions   Orders   Notes

— 200

Chart

| Diabetic 5-Year ▽ | | |
|---|---|---|
| Date | Item | Value |
| 01-01-09 | Health Maintenance | Colon Cancer Screen |
| 01-01-09 | Health Maintenance | Colon Cancer Screen |
| 03-30-06 | RBC | 4.16 |
| 03-30-06 | WBC | 7.5 |
| 03-30-06 | CBC | |
| 03-30-06 | BNP | 42 |
| 03-30-06 | Na | 136 |
| 03-30-06 | K | 4.3 |
| 03-30-06 | Cl | 99 |
| 03-30-06 | Bicarb | 28 |
| 03-30-06 | BUN | 12 |
| 03-30-06 | Creatinine | 0.6 |
| 03-30-06 | HGB | 13 |
| 03-30-06 | SOAP Note | Painful feet |
| 04-30-05 | Outpatient Visit | Painful feet |
| 04-30-05 | A/C Ratio U Microalbumin | 18.3 |
| 02-15-06 | Hemoglobin A1c | 5.6 |
| 02-15-06 | LDL | 116 |
| 02-15-06 | Cholesterol | 202 |
| 02-15-06 | RBC | 4.64 |
| 02-15-06 | WBC | 8.9 |
| 02-15-06 | CBC | |
| 02-15-06 | Glucose | 137 |
| 02-15-06 | INR | 1.1 |

— 230

Search

Items & Values
Dates & Visits
Reference Ranges

☑ Highlight Abnormals   ▽   — 240

| Diabetic Adult | |
|---|---|
| Bicarbonate | 22-26 mEq/L |
| Bilirubin, direct | <0.3 mg/dL |
| Bilirubin, total | 0.2-1.3 mg/dL |
| Calcium | 8.9-10.4 mg/dL |
| Cholesterol | 120-200 mg/dL |
| Creatinine | 0.5-1.4 mg/dL |
| Gamma CT | 8-78 U/L |
| Glucose | 65-110 mg/dL |
| Lipase | 7-60 U/L |

Glucose is normal [between ▽]

65  —△———————△—   110

Reset Profile    Save As New Profile...

— 210

— 220

SYSTEMS AND METHODS FOR USER-CONFIGURABLE RANGE SETTINGS IN CLINICAL INFORMATION SYSTEMS

BACKGROUND OF THE INVENTION

The present invention generally relates to clinical information systems. More specifically, the present invention relates to systems and methods for user-configurable range settings in clinical information systems.

In current healthcare/clinical information systems, healthcare providers may receive lab results or other information pertaining to a patient electronically. A healthcare provider may then review the results to identify abnormal values. In some systems, industry-accepted clinically "normal" values or ranges are used to identify lab results that may need to be brought to the healthcare provider's attention. If a result is out of range, the system alerts the clinician. That is, if a value has fallen outside the normal range for the lab result, the healthcare provider is alerted.

However, many patients may routinely have values that fall outside of the accepted norm. This may be due to a chronic condition, for example. Current systems will flag these values as abnormal, even though they may have become normal for the particular patient. As a result, current systems are ineffective, and even distracting, for the healthcare provider for this particular patient because the healthcare provider will come to ignore the alerts from the system.

For example, the clinically-accepted fasting normal glucose reference range is 70-110 mg/dL. A diabetic patient, however, may consistently have glucose levels of 125 or higher. While this value falls out of the accepted normal range, most clinicians would find a value of 130 for this patient to be unremarkable because of his chronic diabetes. However, a value of 200 would warrant concern and the healthcare provider would desire to be alerted. With current systems, the healthcare provider would receive an alert for both values, even though the value of 130 would be unremarkable for this particular patient.

Current systems do not allow the configuration of a custom range for an individual patient or for a patient population. Thus, there exists a need for systems and methods for user-configurable range settings in clinical information systems.

BRIEF SUMMARY OF THE INVENTION

Certain embodiments of the present invention provide a clinical information system including a user interface and a custom range storage component. The user interface is adapted to allow a user to configure a custom range. The custom range is configured for a lab result. The custom range storage component adapted to store the configured custom range.

Certain embodiments of the present invention provide a user interface including a patient selection component adapted to allow a user to select at least one patient and a custom range component adapted to allow the user to configure a custom range for the selected at least one patient. The custom range is configured for a lab result.

Certain embodiments of the present invention provide a method for alerting a healthcare provider including selecting a patient, configuring a custom range for the patient, and alerting a user when a lab value for the lab result is outside of the custom range. The custom range is configured for a lab result.

Certain embodiments of the present invention provide a computer-readable medium including a set of instructions for execution on a computer, the set of instructions including a patient selection routine, a custom range routine, and an alert routine. The patient selection routine is configured to allow a user to select at least one patient. The custom range routine is configured to allow the user to configure a custom range for the selected at least one patient. The custom range is configured for a lab result. The alert routine is configured to alert a healthcare provider based at least in part on the custom range and a lab value for the lab result.

BRIEF DESCRIPTION OF SEVERAL VIEWS OF THE DRAWINGS

FIG. 2 illustrates a user interface according to an embodiment of the present invention.

Figure 1:
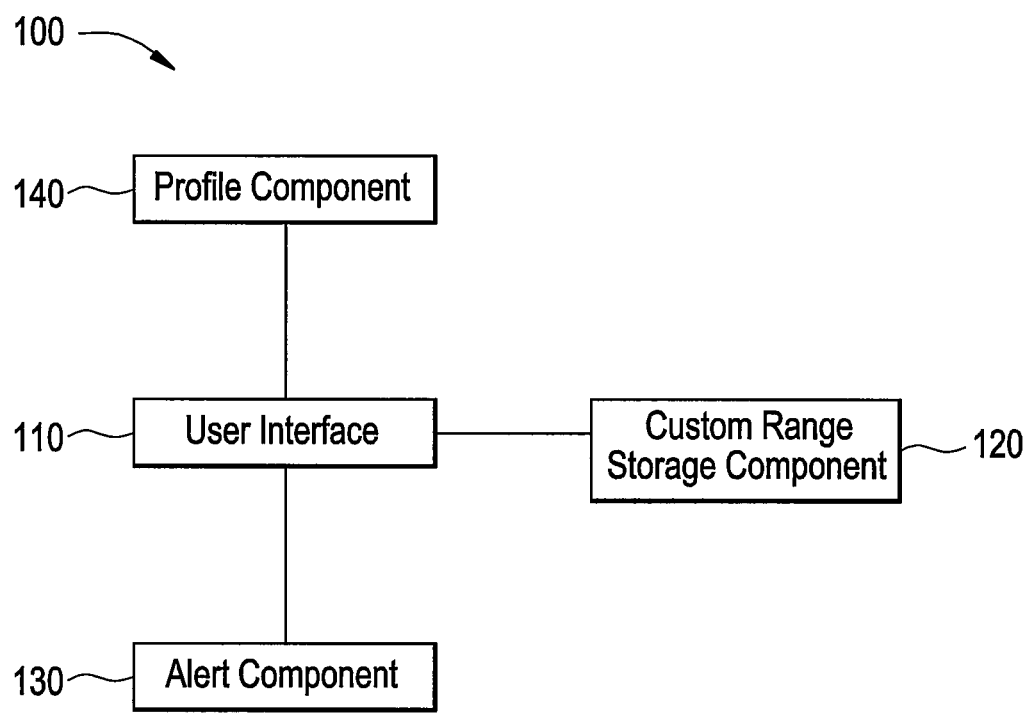
FIG. 1 illustrates a clinical information system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a clinical information system 100 according to an embodiment of the present invention. The system 100 includes a user interface 110, a custom range storage component 120, an alert component 130, and a profile component 140.

The user interface 110 is in communication with the custom range storage component 120, the alert component 130, and the profile component 140.

In operation, the user interface 110 is adapted to allow a user to configure a custom range. The user interface 110 may be part of a clinical information system. The user may be a healthcare provider such as a nurse or physician, for example.

The custom range is for a particular lab result. For example, a custom range may be configured for a lab result for glucose. As another example, a custom range may be configured for a lab result for cholesterol. As another example, a custom range may be configured for blood pressure when a particular patient's blood pressure is not within the clinically-accepted "normal" range so that the healthcare provider is not alerted unnecessarily.

In certain embodiments, the custom range is configured for a period of time or duration. For example, patients taking blood-thinning medications may have a higher-than-normal values for the Prothrombin Time (PT) lab result. The healthcare provider may configure a custom range for the lab result PT for the duration of the prescription of blood thinners for a patient. After the duration has passed, the custom range may revert to a default range, such as a clinically-accepted "normal" range or value.

The custom range may be configured for one or more patients. For example, a custom range for a cholesterol lab result may be configured for a single patient. As another example, a custom range for glucose may be configured for a patient population such as patients with diabetes. The custom range may be configured based at least in part on a disease, such as diabetes, congestive heart failure, or lupus, for example.

The custom range may be used to identify a condition or situation and/or to trigger an action when a lab value for a lab result is inside or outside the range, for example. For example, if the lab value for a glucose lab result is outside of the custom range, a user may be alerted. As another example, if the lab value for blood pressure enters a custom range, a user may be alerted.

The custom range may act as a "normal" range for the patient. For example, a patient with diabetes may have a custom range configured for the glucose lab result that reflects normal glucose lab values for patients with diabetes, as compared to clinically-accepted "normal" values for healthy individuals. Thus, the clinically-accepted "normal" value may be a default range for the patient, and the custom range may be configured to be different from the default range.

The custom range may specify a low value, a high value, or both. That is, a custom range with a high value may indicate that a lab value above the high value is outside of the custom range. Similarly, a custom range with a low value may indicate that a lab value below the low value is outside of the custom range. When the custom range includes both a low value and a high value, a value below the low value or above the high value may be considered out of the custom range. Whether a lab value being inside or outside the custom range is noteworthy may depend on the situation and/or user preference.

In certain embodiments, the user interface 110 is adapted to allow a user to configure more than one custom range for a particular lab result. For example, a user may want to have multiple custom ranges for a lab result. The custom ranges may overlap, for example. The custom ranges may be used to indicate levels of severity, for example. For example, a user may have one custom range for glucose of 90-150 and a second custom range of 70-180. The first custom range may represent a normal range for a specific patient with diabetes, while the second range may represent a tolerable, but perhaps less desirable, range for that patient.

The custom range storage component 120 is adapted to store a configured custom range. The custom range may be configured by the user interface 110, discussed above, for example. The custom range storage component 120 may be part of a clinical information system, for example. For example, the custom range storage component 120 may be integrated into a healthcare information system.

The alert component 130 is adapted to alert a user based at least in part on a custom range. The user may be a healthcare provider such as a nurse or physician, for example. The user is not necessarily the same user that configured the custom range. For example, the custom range may be configured by a physician and the alert component 130 may notify a nurse. The custom range may be configured by the user interface 110, discussed above, for example.

The alert component 130 may alert the user when the lab value for a lab result for a patient falls outside of the custom range configured for the corresponding lab result, for example. For example, a custom range may be configured for Patient X for the lab result "Glucose." The custom range may be 65-150 mg/dL. If a lab value of 200 is received for Patient X for the lab result "Glucose," a user may be alerted that the lab value is outside of the range. As another example, a user may be alerted when the lab value falls within the custom range.

The alert component 130 may alert the user in a variety of ways. For example, the alert component 130 may display the lab result to the user in a different color. As another example, the alert component 130 may notify the user via an email, page, or pop-up window. When more than one custom range is configured for a particular lab result, the alert component 130 may alert a user by one mechanism when the lab value falls outside of one custom range, but not another, for example.

The profile component 140 is adapted to store a set of custom ranges. The set of custom ranges may be part of a profile, for example. The set of custom ranges includes one or more custom ranges. Each custom range in the set may be configured for a different lab result. For example, a set of custom ranges may include a custom range for the lab result "Glucose" and the lab result "Cholesterol." As another example, a set of custom ranges may include two custom ranges for the lab result "Glucose."

The profile component 140 may be utilized by the user interface 110 to associate a set of custom ranges with a particular patient or population. For example, a set of custom ranges may be configured for a single patient. As another example, a profile for a diabetic may be configured for a patient population such as patients with diabetes. The profile may be configured based at least in part on a disease, such as diabetes, congestive heart failure, or lupus, for example.

FIG. 2 illustrates a user interface 200 according to an embodiment of the present invention. The user interface 200 includes a custom range component 210, a patient selection component 220, an alert component 230, and a profile selection component 240.

The user interface 200 may be similar to the user interface 110, discussed above, for example.

In operation, a user, such as a healthcare provider, configures a custom range using the custom range component 210. That is, the custom range component 210 is adapted to allow a user to configure a custom range. The custom range may be similar to the custom range discussed above, for example. The custom range may be configured for one or more patients selected by the patient selection component 220, discussed below, for example.

The custom range is for a particular lab result. For example, a custom range may be configured for a lab result for glucose. As another example, a custom range may be configured for a lab result for cholesterol. As another example, a custom range may be configured for blood pressure when a particular patient's blood pressure is not within the clinically-accepted "normal" range so that the healthcare provider is not alerted unnecessarily.

In certain embodiments, the custom range is configured for a period of time or duration. For example, patients taking blood-thinning medications may have a higher-than-normal values for the Prothrombin Time (PT) lab result. The healthcare provider may configure a custom range for the lab result PT for the duration of the prescription of blood thinners for a patient. After the duration has passed, the custom range may revert to a default range, such as a clinically-accepted "normal" range or value.

The custom range may act as a "normal" range for the patient. For example, a patient with diabetes may have a custom range configured for the glucose lab result that reflects normal glucose lab values for patients with diabetes, as compared to clinically-accepted "normal" values for healthy individuals. Thus, the clinically-accepted "normal" value may be a default range for the patient, and the custom range may be configured to be different from the default range.

The custom range may specify a low value, a high value, or both. That is, a custom range with a high value may indicate that a lab value above the high value is outside of the custom range. Similarly, a custom range with a low value may indicate that a lab value below the low value is outside of the custom range. When the custom range includes both a low value and a high value, a value below the low value or above the high value may be considered out of the custom range. Whether a lab value being inside or outside the custom range is noteworthy may depend on the situation and/or user preference.

In certain embodiments, the custom range component 210 is adapted to allow a user to configure more than one custom range for a particular lab result. For example, a user may want to have multiple custom ranges for a lab result. The custom ranges may overlap, for example. The custom ranges may be used to indicate levels of severity, for example. For example, a user may have one custom range for glucose of 90-150 and a second custom range of 70-180. The first custom range may represent a normal range for a specific patient with diabetes, while the second range may represent a tolerable, but perhaps less desirable, range for that patient.

The patient selection component 220 is adapted to allow a user to select at least one patient. The patients may be selected from a list of available patients, for example. As another example, the patients may be selected by name, disease, type, or other characteristic. For example, a physician may select all of the patients for which the physician is the primary care physician.

In certain embodiments, the patient selection component 220 is adapted to allow the user to select a patient population. For example, the user may select the population of patients with diabetes.

In certain embodiments, the patient selection component 220 is adapted to allow the user to select at least one patient based at least in part on a disease, such as diabetes, congestive heart failure, or lupus, for example.

The alert component 230 is adapted to alert a user when a lab value for a lab result is outside of a custom range. The alert component 230 may be similar to the alert component 130, discussed above, for example. The user may be a healthcare provider such as a nurse or physician, for example. The user is not necessarily the same user that configured the custom range. For example, the custom range may be configured by a physician and the alert component 230 may notify a nurse. The custom range may be configured by the custom range component 210, discussed above, for example.

The alert component 230 may alert the user when the lab value for a lab result for a patient falls outside of the custom range configured for the corresponding lab result, for example. For example, a custom range may be configured for Patient X for the lab result "Glucose." The custom range may be 65-150 mg/dL. If a lab value of 200 is received for Patient X for the lab result "Glucose," a user may be alerted that the lab value is outside of the range. As another example, a user may be alerted when the lab value falls within the custom range.

The alert component 230 may alert the user in a variety of ways. For example, the alert component 230 may display the lab result to the user in a different color. As another example, the alert component 230 may notify the user via an email, page, or pop-up window. When more than one custom range is configured for a particular lab result, the alert component 230 may alert a user by one mechanism when the lab value falls outside of one custom range, but not another, for example.

The profile selection component 240 is adapted to allow a user to select a profile to be associated with a patient. The profile may include a set of custom ranges, for example. The set of custom ranges includes one or more custom ranges. Each custom range in the set may be configured for a different lab result. For example, a set of custom ranges may include a custom range for the lab result "Glucose" and the lab result "Cholesterol." As another example, a set of custom ranges may include two custom ranges for the lab result "Glucose." The profile may be configured based at least in part on a disease, such as diabetes, congestive heart failure, or lupus, for example.

In certain embodiments, the profile selection component 240 is adapted to allow the user to select a profile to be associated with a particular patient. For example, a profile including a set of custom ranges may be configured for a single patient.

In certain embodiments, the profile selection component 240 is adapted to allow the user to select a profile to be associated with a patient population. For example, a profile for a diabetic may be configured for a patient population such as patients with diabetes.

The components, elements, and/or functionality of the system 100 and/or the user interface 200 may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device.

Figure 3:
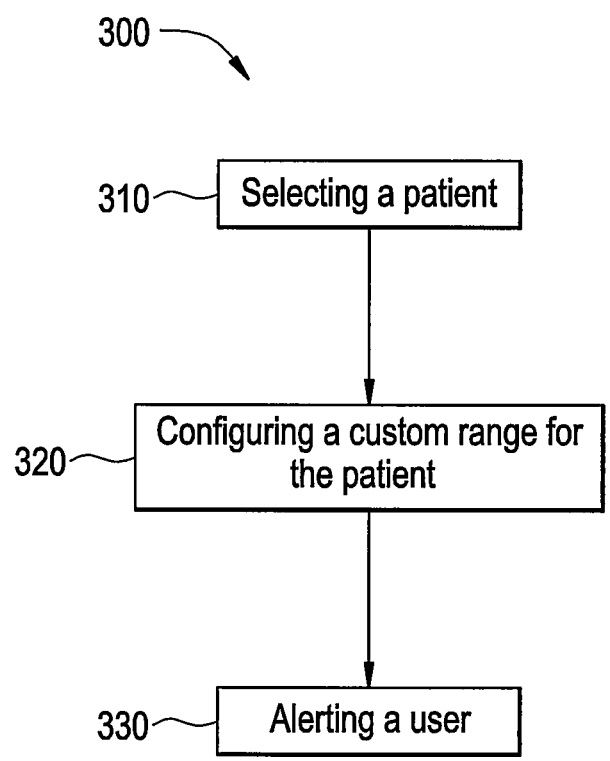
FIG. 3 illustrates a flow diagram for a method for alerting a healthcare provider according to an embodiment of the present invention.

FIG. 3 illustrates a flow diagram for a method 300 for alerting a healthcare provider according to an embodiment of the present invention. The method 300 includes the following steps, which will be described below in more detail. At step 310, a patient is selected. At step 320, a custom range is configured for the patient. At step 330, a user is alerted. The method 300 is described with reference to elements of systems described above, but it should be understood that other implementations are possible.

At step 310, a patient is selected. The patient may be selected by a user. The user may be a healthcare provider such as a nurse or physician, for example. The patient may be selected using a user interface similar to the user interface 110 and/or the user interface 200, described above, for example. The patient may be selected using a patient selection component similar to the patient selection component 220, described above, for example.

At least one patient may be selected. That is, a single patient may be selected. Alternatively, more than one patient may be selected. The patients may be selected from a list of available patients, for example. As another example, the patients may be selected by name, disease, type, or other characteristic.

In certain embodiments, the patient selected is part of a patient population. For example, the user may select the population of patients with diabetes. In certain embodiments, the patient is selected based at least in part on a disease, such as diabetes, congestive heart failure, or lupus, for example.

At step 320, a custom range is configured for the patient. The custom range may be configured by a user. The user may be a healthcare provider such as a nurse or physician, for example. The custom range may be configured by and/or using a user interface similar to the user interface 110 and/or the user interface 200, described above, for example. The custom range may be configured by and/or using a custom range component similar to the custom range component 210, described above, for example. The patient may be the patient selected at step 310, described above, for example. The custom range may be similar to the custom range discussed above, for example.

The custom range is for a particular lab result. For example, a custom range may be configured for a lab result for glucose. As another example, a custom range may be configured for a lab result for cholesterol. As another example, a custom range may be configured for blood pressure when a particular patient's blood pressure is not within the clinically-accepted "normal" range so that the healthcare provider is not alerted unnecessarily.

In certain embodiments, the custom range is configured for a period of time or duration. For example, patients taking blood-thinning medications may have a higher-than-normal values for the Prothrombin Time (PT) lab result. The healthcare provider may configure a custom range for the lab result PT for the duration of the prescription of blood thinners for a patient. After the duration has passed, the custom range may revert to a default range, such as a clinically-accepted "normal" range or value.

The custom range may act as a "normal" range for the patient. For example, a patient with diabetes may have a custom range configured for the glucose lab result that reflects normal glucose lab values for patients with diabetes, as compared to clinically-accepted "normal" values for healthy individuals. Thus, the clinically-accepted "normal" value may be a default range for the patient, and the custom range may be configured to be different from the default range.

The custom range may specify a low value, a high value, or both. That is, a custom range with a high value may indicate that a lab value above the high value is outside of the custom range. Similarly, a custom range with a low value may indicate that a lab value below the low value is outside of the custom range. When the custom range includes both a low value and a high value, a value below the low value or above the high value may be considered out of the custom range. Whether a lab value being inside or outside the custom range is noteworthy may depend on the situation and/or user preference.

In certain embodiments, the custom range is part of a set of custom ranges. The set of custom ranges may be part of a profile, for example. The set of custom ranges includes one or more custom ranges. Each custom range in the set may be configured for a different lab result. For example, a set of custom ranges may include a custom range for the lab result "Glucose" and the lab result "Cholesterol." As another example, a set of custom ranges may include two custom ranges for the lab result "Glucose." The profile may be stored by a profile component similar to the profile component 140, discussed above, for example. The profile may be selected by a profile selection component similar to the profile selection component 240, discussed above, for example.

The set of custom ranges may be configured to be associated with a particular patient or population. For example, a set of custom ranges may be configured for a single patient. As another example, a profile for a diabetic may be configured for a patient population such as patients with diabetes. The profile may be configured based at least in part on a disease, such as diabetes, congestive heart failure, or lupus, for example.

In certain embodiments, more than one custom range is configured for a particular lab result. For example, a user may want to have multiple custom ranges for a lab result. The custom ranges may overlap, for example. The custom ranges may be used to indicate levels of severity, for example.

At step 330, a user is alerted. The user may be a healthcare provider such as a nurse or physician, for example. The user is not necessarily the same user that configured the custom range at step 320, described above. For example, the custom range may be configured by a physician and a nurse may be notified. The user may be alerted by an alert component similar to the alert component 130 and/or the alert component 230, described above, for example.

The user may be alerted when a lab value for a lab result is outside of a custom range. The custom range may be the custom range configured at step 320, described above, for example. The user may be alerted when the lab value for a lab result for a patient falls outside of the custom range configured for the corresponding lab result, for example. For example, a custom range may be configured for Patient X for the lab result "Glucose." The custom range may be 65-150 mg/dL. If a lab value of 200 is received for Patient X for the lab result "Glucose," a user may be alerted that the lab value is outside of the range. As another example, a user may be alerted when the lab value falls within the custom range.

The user may be alerted in a variety of ways. For example, the lab result may be displayed to the user in a different color. As another example, the user may be notified via an email, page, or pop-up window. When more than one custom range is configured for a particular lab result, the a user may be alerted by one mechanism when the lab value falls outside of one custom range, but not another, for example.

One or more of the steps of the method 300 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide systems and methods for user-configurable range settings in clinical information systems. Certain embodiments provide a technical effect of user-configurable range settings in clinical information systems.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A clinical information system, the system including:
a user interface operably connected to a computer processor, the user interface and processor being part of the clinical information system used in connection with providing healthcare services, the user interface adapted to allow a user to configure a custom range for a lab result for a patient population; and a custom range storage component operably connected to the processor, the custom range storage component adapted to use the processor to store the configured custom range; and wherein the user interface is adapted to allow a second custom range to be configured for the lab result, the custom range being a normal range for the lab result and the second custom range being an acceptable but less desirable range for the lab result.

2. The system of claim 1, wherein the user interface is adapted to allow the user to associate the custom range with a patient population that is indicated to have a certain disease.

3. The system of claim 1, wherein the custom range represents a normal range for the lab result.

4. The system of claim 1, wherein the custom range is different from a default range.

5. The system of claim 1, wherein the custom range specifies only a high value.

6. The system of claim 1, wherein the custom range specifies only a low value.

7. The system of claim 1, further including an alert component adapted to alert a healthcare provider based at least in part on the custom range and a lab value for the lab result.

8. The system of claim 1, further including a profile component adapted to allow a profile including a plurality of custom lab result ranges to be associated with the patient population.

9. The system of claim 8, wherein the plurality of custom lab result ranges includes the custom range for the lab result and a second custom range for a second lab result.

10. A clinical information system, the system including:
a user interface operably connected to a computer processor, the user interface and processor being part of the clinical information system used in connection with providing healthcare services, the user interface adapted to allow a user to configure a custom range for a lab result for a patient population; and a custom range storage component operably connected to the processor, the custom range storage component adapted to use the processor to store the configured custom range;

wherein the user interface is adapted to allow the user to configure the custom range to be applied for a limited duration.

11. The system of claim 10, wherein the user interface is adapted to allow the user to associate the custom range with a patient population that is indicated to have a certain disease.

12. The system of claim 10, wherein the custom range represents a normal range for the lab result.

13. The system of claim 10, wherein the custom range is different from a default range.

14. The system of claim 10, wherein the custom range specifies only a high value.

15. The system of claim 10, wherein the custom range specifies only a low value.

16. The system of claim 10, further including an alert component adapted to alert a healthcare provider based at least in part on the custom range and a lab value for the lab result.

17. The system of claim 10, further including a profile component adapted to allow a profile including a plurality of custom lab result ranges to be associated with the patient population 18. The system of claim 17, wherein the plurality of custom lab result ranges includes the custom range for the lab result and a second custom range for a second lab result.

* * * * *